United States Patent [19]
Graves et al.

[11] Patent Number: 4,501,741
[45] Date of Patent: Feb. 26, 1985

[54] CEPHALOSPORIN ANTIBIOTICS

[75] Inventors: Bernard J. Graves, Indianapolis; Stjepan Kukolja, Carmel, both of Ind.

[73] Assignee: Eli Lilly and Company, Indianapolis, Ind.

[21] Appl. No.: 484,125

[22] Filed: Apr. 12, 1983

[51] Int. Cl.³ .................. C07D 501/22; C07D 501/58
[52] U.S. Cl. ..................... 514/202; 544/22; 544/28
[58] Field of Search ..................... 424/246; 544/22, 28

[56] References Cited

U.S. PATENT DOCUMENTS

| | | | |
|---|---|---|---|
| 3,575,969 | 4/1971 | Morin et al. | 544/28 |
| 4,024,133 | 5/1977 | Cook et al. | 544/30 |
| 4,219,648 | 8/1980 | Edwards | 544/28 |
| 4,229,575 | 10/1980 | Böhme | 544/27 |

Primary Examiner—Paul M. Coughlan, Jr.
Attorney, Agent, or Firm—William B. Scanlon; Arthur R. Whale

[57] ABSTRACT

7β-[2-Amino-2-(benzothien-4,5,6, and 7-yl)acetylamino]-3-substituted-3-cepham-4-carboxylic acids and 7β-[2-amino-2-(2,3-dihydrobenzothien-4,5,6, and 7 yl)acetylamino]-3H- or 3-substituted-3-cephem-4-carboxylic acids (1), e.g. 7β-[2-amino-2-(benzothien-4-yl)acetylamino]-3-methyl-3-cephem-4-carboxylic acid, are orally effective antibiotics. Also provided are benzothienyl oximino compounds, the corresponding 2,3-dihydro compounds (2) useful as intermediates to (1) and as antibiotics, as well as 7β-(2,2-dialkyl-5-oxo-4-benzothienyl-1-imidazolidinyl)-3H-(3-substituted)-3-cephem-4-carboxylic acids and the corresponding 2,3-dihydro compounds (3) useful as antibiotics, and prepared with (1) by condensation with ketones. Pharmaceutical formulations of antibiotic compounds (1), (2), and (3) are provided.

13 Claims, No Drawings

CEPHALOSPORIN ANTIBIOTICS

BACKGROUND OF THE INVENTION

Among the clinically used cephalosporin antibiotics, only a few exhibit significant absorption from the gut and are therapeutically useful when administered orally. Cephalexin and cefaclor are two orally effective cephalosporin antibiotics that are highly absorbed. The majority of the cephalosporin antibiotics, however, are effective when administered parenterally. Considerable research work by chemists and microbiologists is directed toward the discovery and development of new orally effective semi-synthetic cephalosporin antibiotics with improved properties, for example, enhanced activity against staphylococci and streptococci, effectiveness against resistant microorganisms, and high absorptivity from the gut.

SUMMARY

This invention relates to 7β-[2-amino-2-(benzothien-4-yl)acetylamino]-3-substituted (or unsubstituted)-3-cephem-4-carboxylic acids, the benzothien-5-yl, benzothien-6-yl, and benzothien-7-yl isomers, and the salts and 2,3-dihydro derivatives thereof. The compounds are useful orally effective antibiotics, eg. 7β-[2-amino-2-(benzothien-4-yl)acetylamino]-3-methyl-3-cephem-4-carboxylic acid is effective against gram-positive and anaerobic bacteria when administered by the oral route. The compounds are prepared by the N-acylation of a 7-amino-3-cephem nucleus compound with an amino-protected benzothienylglycine, a dihydrobenzothienylglycine, or an active derivative thereof.

The invention also provides intermediates useful in the preparation of the antibiotics and pharmaceutical formulations comprising the antibiotics.

DETAILED DESCRIPTION

This invention provides cephalosporin antibiotics represented by the following formula 1

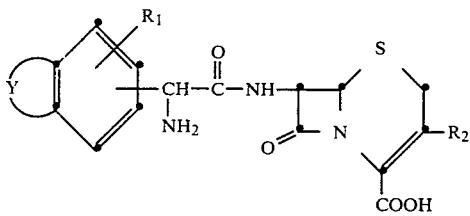

wherein Y is

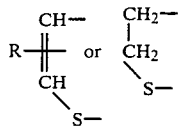

R is hydrogen, $C_1-C_3$ alkyl, halogen, nitro, amino, $C_1-C_4$ alkoxy, $C_1-C_4$ alkanoylamino, or $C_1-C_3$ alkylsulfonylamino;

$R_1$ is hydrogen, $C_1-C_3$ alkyl, halogen, hydroxy, or $C_1-C_4$ alkoxy;

$R_2$ is hydrogen, methyl, halogen, methoxy, vinyl, or a substituted methyl group represented by the formula

—$CH_2$—$R_2'$ wherein $R_2'$ is methoxy, acetoxy, or carbamoyloxy; and the pharmaceutically acceptable non-toxic salts thereof.

In the above formula halogen refers to fluoro, chloro, or bromo; $C_1-C_3$ alkyl refers to methyl, ethyl, n-propyl, and isopropyl; and $C_1-C_4$ alkoxy refers to methoxy, ethoxy, n-propoxy, iso-propoxy, n-butoxy, iso-butoxy, and t-butoxy.

The compounds of the formula 1, having the glycyl moiety with an asymmetric carbon atom, can exist as the D,L-racemate or as the individual D- or L-isomer. The compounds also can exist in the internal salt form or zwitterionic form represented by the formula

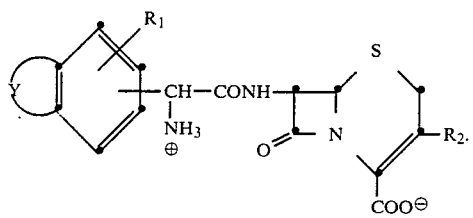

As is shown in the formula 1, the compounds of the invention may be characterized by the nature of the bonding in the glycyl side chain. The glycyl moiety —CH($NH_2$)—CO— is bonded to a carbon of the benzene ring of the benzothienyl heterocyclic rather than to a carbon of the thienyl hetero ring or the dihydrothienyl ring.

Pharmaceutically-acceptable salts of the formula 1 compounds include the acid addition salts of the amino group such as the hydrochloride and hydrobromide salts, as well as the salts formed with the carboxy group such as the alkali metal and alkaline earth metal salts eg. sodium, potassium, and calcium salts. Likewise, the ammonium and substituted ammonium salts can be used, for example, the benzylammonium, dibenzylammonium, 2-hydroxyethylammonium, di-(2-hydroxyethyl)ammonium, cyclohexylammonium, dicyclohexylammonium, methylammonium, diethylammonium, dipropylammonium and like ammonium salts formed with ammonia and primary and secondary amines. Other amine salts may also be used such as those formed with procaine and abietylamine.

Examples of compounds of the invention represented by the formula 1 wherein Y is —S—CH=CH— are:
- 7β-[2-amino-2-(benzothien-4-yl)acetylamino]-3-methyl-3-cephem-4-carboxylic acid,
- 7β-[2-amino-2-(benzothien-5-yl)acetylamino]-3-methyl-3-cephem-4-carboxylic acid,
- 7β-[2-amino-2-(benzothien-4-yl)acetylamino]-3-chloro-3-cephem-4-carboxylate,
- 7β-[2-amino-2-(benzothien-6-yl)acetylamino]-3-methoxy-3-cephem-4-carboxylate,
- 7β-[2-amino-2-(benzothien-5-yl)acetylamino]-3-methoxymethyl-3-cephem-4-carboxylic acid,
- 7β-[2-amino-2-(benzothien-7-yl)acetylamino]-3-methyl-3-cephem-4-carboxylic acid,
- 7β-[2-amino-2-(benzothien-4-yl)acetylamino]-3-acetoxymethyl-3-cephem-4-carboxylic acid,
- 7β-[2-amino-2-(7-hydroxybenzothien-4-yl)acetylamino]-3-methyl-3-cephem-4-carboxylic acid, 7β-[2-amino-2-(6-hydroxybenzothien-4-yl)acetylamino]-3-methyl-3-cephem-4-carboxylic acid, 7β-[2-amino-2-(4-hydroxybenzothien-7-yl)acetylamino]-3-chloro-3-cephem-4-carboxylic acid, 7β-[2-amino-2-(5-chlorobenzothien-4-yl)acetylamino]-3-methoxy-3-cephem-4-carboxylic acid, 7β-[2-amino-2-(6-methylbenzothien-7-yl)acetylamino]-3-bromo-3-cephem-4-carboxylic acid, 7β-[2-amino-2-(7-methoxybenzothien-4-yl)acetylamino]-3-methyl-3-cephem-4-carboxylic acid, 7β-[2-amino-2-(7-methoxybenzothien-4-yl)acetylamino]-3-acetoxymethyl-3-cephem-4-carboxylic acid, 7β-[2-amino-2-(benzothien-6-yl)acetylamino]-3-methyl-3-cephem-4-carboxylic acid, 7β-[2-(benzothien-4-yl)-3-cephem-4-carboxylic acid, 7β-[2-amino-2-(2-aminobenzothien-4-yl)acetylamino]-3-methyl-3-cephem-4-carboxylic acid, 7β-[2-amino-2-(2-acetylaminobenzothien-7-yl)acetylamino]-3-methoxy-cephem-4-carboxylic acid, 7β-[2-amino-2-(3-methylsulfonylaminobenzothien-5-yl)acetylamino]-3-methyl-3-cephem-4-carboxylic acid, and 7β-[2-amino-2-(benzothien-4-yl)acetylamino]-3-carbamoyloxymthyl-3-cephem-4-carboxylic acid.

Examples of dihydrobenzothienyl cephalosporins of the invention, wherein formula 1 Y is —S—CH$_2$—CH$_2$—, are represented by the following formula

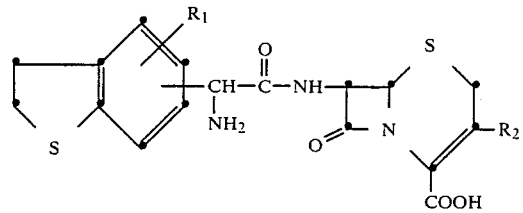

| R$_1$ | R$_2$ | isomer |
|---|---|---|
| H | CH$_3$ | 4-yl |
| H | CH$_3$ | 6-yl |
| CH$_3$ | H | 4-yl |
| H | Cl | 4-yl |
| H | OCH$_3$ | 5-yl |
| Cl | acetoxymethyl | 4-yl |
| CH$_3$O | carbamoyloxymethyl | 5-yl |
| Cl | CH$_3$ | 4-yl |
| Br | CH$_3$ | 7-yl |
| H | CH$_3$OCH$_2$ | 5-yl |

A preferred group of compounds of the formula 1 are represented when Y is —S—CH=CH— and R and R$_1$ are hydrogen and R$_2$ is methyl, methoxy, or chloro. Another preferred group is represented when R is hydrogen, methyl, or chloro, R$_1$ is hydrogen, hydroxy, methoxy or ethoxy.

The compounds of the invention represented by the formula 1 can be prepared by various routes. One route comprises the N-acylation of a 7-amino nucleus compound represented by the formula

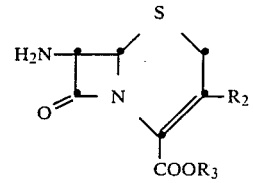

wherein R$_2$ has the same meaning as defined for formula 1 and R$_3$ is a carboxy protecting group, with the amino-protected benzothienylglycyl or dihydobenzothienylglycyl compound represented by the formula

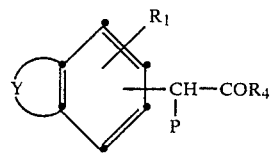

wherein Y, R and R$_1$ have the same meanings as defined for formula 1, P is a protected amino group and R$_4$ is hydroxy, halogen, azido, or the residue of an active ester or mixed anhydride.

The amino-protected and esterified acylation product represented by the formula

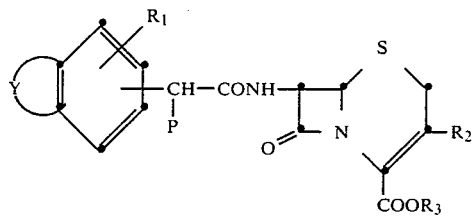

is deprotected and deesterified to the compound 1.

Examples of carboxy-protecting groups R$_3$ are the conventional protecting groups such as for example t-butyl, 2-iodoethyl, methoxymethyl, allyl, 2,2,2-trihaloethyl, benzyl, substituted benzyl such as p-methoxybenzyl, p-nitrobenzyl, p-methylbenzyl, and diphenylmethyl, trialkylsilyl such as trimethylsilyl, and like protecting groups. Examples of active ester groups R$_4$ are esters formed with N-hydroxy heterocyclics such as hydroxybenzotriazole, hydroxytriazole, N-hydroxysuccinimide and the like. Anhydrides of the benzothienylglycine useful in the N-acylation are those formed with the chloroformates such as methyl chloroformate, ethyl chloroformate or isobutyl chloroformate.

During the acylation the amino group of the benzothienylglycine or the dihydro derivative thereof is desirably protected to prevent its acylation in competition with the 7-amino nucleus. Useful amino-protecting groups are those commonly employed for the temporary protection of amino groups in the β-lactam antibiotics art. Examples of such groups are the active methylene compounds such as methyl acetoacetate and ethyl acetoacetate which form enamines with the amine; the alkoxycarbonyl halides, substituted alkoxycarbonyl halides and alkenyloxycarbonyl halides such as the C$_1$-C$_4$ alkoxycarbonyl chlorides eg. ethoxycarbonyl chloride, t-butoxycarbonyl chloride, trichloroethoxycarbonyl chloride, benzyloxycarbonyl chloride, p- nitrobenzyloxycarbonyl chloride and allyloxycarbonyl chloride; bicyclic carbonyl chlorides such as adamantyloxycarbonyl chloride; and cycloaliphatic carbonyl chlorides such as cyclopentyloxycarbonyl chloride and cyclohexyloxycarbonyl chloride.

Those skilled in the art will appreciate that when R in the formula 1 is an amino group it is likewise desirably protected during the acylation to prevent unwanted N-acylation at this amino group. Any of the above-mentioned amino-protecting groups can serve for the temporary protection of compounds wherein R is amino.

The acylation can be carried out with the amino group protected as the salt eg. the hydrochloride salt. For example, the benzothienylglycyl chloride hydrochloride is used to acylate the 7-amino nucleus as a silyl ester eg. the trimethylsilyl ester. After the acylation is complete, the silyl ester is hydrolyzed and the product obtained as the free amine free acid at its isoelectric point. The above acylation method is illustrated by the following reaction scheme wherein 7ADCA trimethylsilyl ester is acylated with 2-amino-2-(benzothien-4-yl)acetyl chloride hydrochloride.

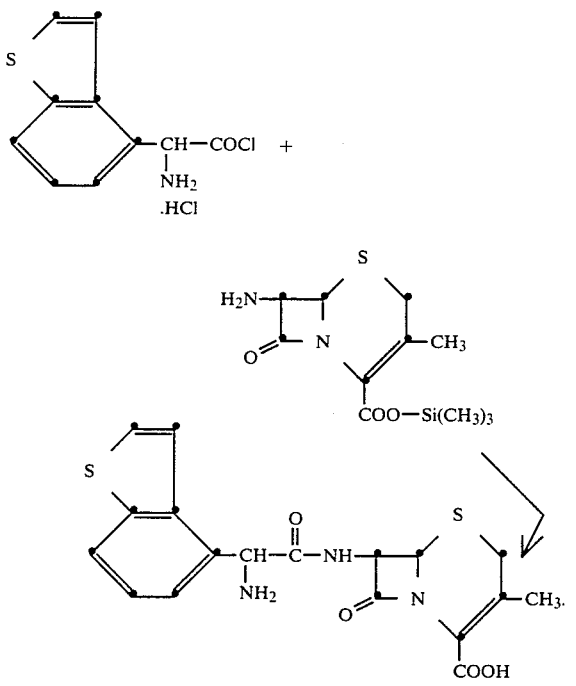

The amino-protected benzothienylglycine or the dihydro derivative thereof as the free acid ($R_4$=OH) can be used to N-acylate the 7-amino nucleus by coupling the acid and the amine with a dehydrating agent. Dehydrating coupling reagents which can be used are for example, the carbodiimides such as dicyclohexylcarbodiimide and dibutylcarbodiimide; and the common coupling reagent EEDQ (1-ethoxycarbonyl-2-ethoxy-1,2-dihydroquinoline). For example, 2-t-butyloxycarbamido-2-(benzothien-5-yl)acetic acid is reacted in a dry inert organic solvent such as acetonitrile with p-nitrobenzyl 7-amino-3-chloro-3-cephem-4-carboxylate in the presence of excess EEDQ to provide p-nitrobenzyl 7β-[2-(t-butyloxycarbonylamino)-2-(benzothien-5-yl)acetylamino]-3-chloro-3-cephem-4-carboxylate. The product is reduced with zinc and acetic acid to remove the p-nitrobenzyl ester group and the amino-protecting group is removed on treatment of the acid with trifluoroacetic acid.

The 7-amino nucleus compounds used in the acylation are known and can be prepared by well-known procedures. 7ADCA ($R_2$=$CH_3$) is described by Stedman, *J. Med. Chem.*, 7, 117 (1964) and by Chauvette et al., *J. Org. Chem.*, 36, 1259 (1971); the 3-halo nucleus and the 3-methoxy nucleus ($R_2$=X or $OCH_3$) are described by Chauvette in U.S. Pat. Nos. 4,064,343 and 3,917,587 respectively; and the 3-vinyl nucleus ($R_2$=—CH=$CH_2$) is described in U.S. Pat. No. 3,994,884.

The compounds of the formula 1 wherein $R_2$ is methyl also can be prepared by the N-acylation of 7-amino-3-exomethylenecepham-4-carboxylic acid esters (U.S. Pat. No. 3,932,393) followed by isomerization of the 3-exocepham to the 3-cephem (exo to endo). The N-acylation of the 3-exomethylenecepham nucleus is carried out by any of the N-acylation methods described hereinabove. For example, 2-(t-butyloxycarbonylamino)-2-(benzothien-6-yl)acetic acid is converted to the anhydride formed with methyl chloroformate in the presence of triethylamine, and the anhydride formed is reacted with p-nitrobenzyl 7-amino-3-exomethylenecepham-4-carboxylate as shown below

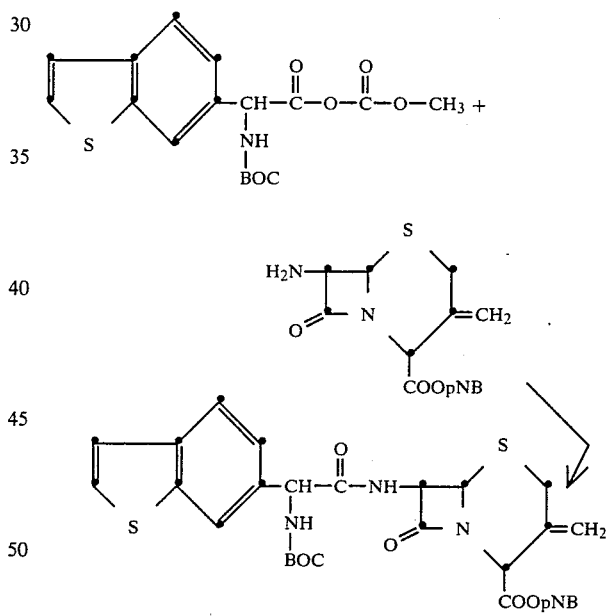

wherein BOC is t-butyloxycarbonyl and pNB is p-nitrobenzyl. The product is then treated with a mixture of a highly polar aprotic solvent such as dimethylacetamide and a tertiary amine such as triethylamine to provide, via isomerization of the 3-exo double bond, the corresponding 3-methyl-3-cephem ester. The pNB ester is removed by reduction with zinc and acetic acid and the BOC group removal is accomplished with trifluoroacetic acid.

The compounds of the formula 1 wherein $R_2$ is halo or methoxy likewise can be obtained by an alternative process. This alternative process employs in the acylation a 7-amino-3-hydroxy-3-cephem-4-carboxylic acid ester represented by the formula

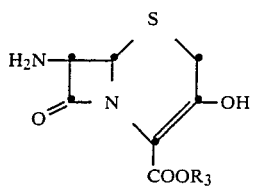

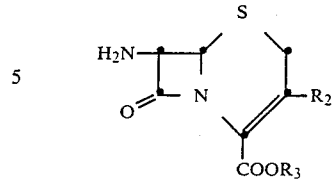

wherein $R_3$ has the same meanings as defined hereinabove. The acylation of the 3-hydroxy nucleus ester with an amino-protected benzothienylglycine or dihydro derivative thereof is carried out in the presence of some water to prevent the competitive 3-hydroxy acylation which can occur under anhydrous acylation conditions (U.S. Pat. No. 3,917,587). Following acylation, the 3-hydroxy group is converted to the 3-methoxy group with diazomethane or to the 3-halo compound as described by U.S. Pat. No. 4,064,343. After the methylation or halogenation, the ester group and the amino-protecting group are removed to provide the desired 3-halo or 3-methoxy compound.

In yet a further method for preparing compounds of the invention wherein $R_2$ is methyl, methoxy, or chloro, a 7-aminocephalosporanic acid ester is acylated with the desired benzothienylglycine or dihydrobenzothienyl glycine and the product is reacted with a thiol such as a $C_1$–$C_4$ alkyl mercaptan or with thiourea to form, the 3-alkylthio or isothiouronium derivative, respectively, by nucleophilic displacement of the 3-acetoxy group. The thio derivative is then subjected to reductive displacement with Raney nickel and hydrogen or with zinc and formic acid in DMF to provide the 3-exomethylenecepham compound. The latter is then isomerized to the 3-methyl-3-cephem as described hereinabove. The 3-exomethylenecepham can be reacted with ozone in the cold to provide the 3-hydroxy-3-cephem and the latter converted to the 3-halo or 3-methoxy compound as described hereinabove. The above-described conversion of the 3-acetoxymethyl compound to the 3-exomethylenecepham is carried out according to the methods described by Chauvette in U.S. Pat. No. 3,932,393.

The compounds represented by the formula 1 also can be obtained by yet a further general preparative method. According to this method, a 2-(benzothienyl)-2-oximino (or alkoximino)acetic acid or dihydro derivative thereof represented by the formula

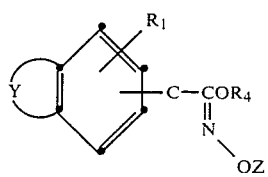

wherein $R_4$ has the previously defined meanings, is used to N-acylate a 7-amino nucleus compound to provide a 7β-[2-(benzothienyl or dihydrobenzothienyl)-2-oximino (or alkoxyimino)acetylamino]-3H or (3-substituted)-3-cephem-4-carboxylic acid ester represented by the formula 2.

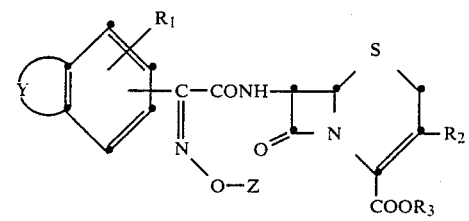

In the formula 2, Y, R, $R_1$, $R_2$, and $R_3$ have the same meanings as defined hereinabove and Z is hydrogen or $C_1$–$C_4$ alkyl. The acylation is carried out by the methods described previously herein for the N-acylation of a 7-amino nucleus compound with an amino-protected benzothienylglycine. The oximino group is then reduced to the amino group and the ester group removed to provide a compound of the formula 1. The reduction can be carried out chemically or by catalytic hydrogenation. Chemical reduction is preferred, for example, with zinc and an acid such as formic acid or acetic acid.

According to a further aspect of this invention, the oximino esters represented by the above formula 2, the free acids obtained by deesterification of the esters, and certain derivatives thereof are provided. The oximino compounds provided are represented by the following formula 3

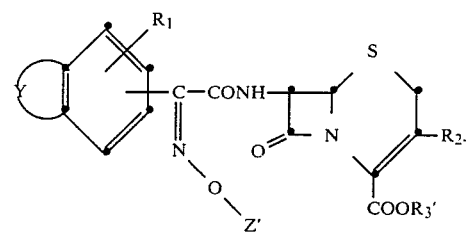

In the above formula 3 Y, R, $R_1$, and $R_2$ have the same meanings as defined for formula 1; $R_3'$ is hydrogen or a carboxy-protecting group; Z' is hydrogen, $C_1$–$C_4$ alkyl, or a carboxy-substituted alkyl or carboxy-substituted cycloalkyl group represented by the formula

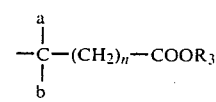

wherein $R_3'$ has the same meanings as above, a and b independently are hydrogen or $C_1$–$C_3$ alkyl or a and b taken together with the carbon to which they are bonded form a $C_3$–$C_6$ cycloalkyl ring, and n is 0 to 3;

and when $R_3'$ is hydrogen the pharmaceutically acceptable non-toxic salts thereof.

The compounds of the formula 2 wherein $Z'$ is hydrogen or $C_1$–$C_4$ alkyl, and $R_3'$ is a carboxy-protecting group are useful intermediates in the preparation of the formula 1 compounds. The compounds of formula 3 wherein $R_3'$ (both occurrences) is hydrogen or the pharmaceutically acceptable salts thereof possess antibacterial activity and are useful in controlling the growth of microorganisms pathogenic to man and animals. The latter compounds possess inhibitory activity vs. a broader spectrum of microorganisms than do the formula 1 compounds. The oximino free acids 3 and the salt forms thereof possess activity vs. the gram-negative and gram-positive bacteria such as staphylococcus, streptococcus, salmonella, proteus, E. coli, and klebsiella.

The compounds represented by the formula 3 wherein $Z'$ is a carboxy-substituted alkyl or cycloalkyl group are prepared with the compounds wherein $Z'$ is hydrogen. The free hydroxime is alkylated with a carboxy-substituted alkyl halide represented by the formula

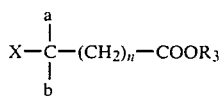

wherein X is chloro or bromo, $R_3$ is a carboxy-protecting group as defined hereinabove, and a, b, and n are as defined for formula 3. The alkylation is carried out under anhydrous conditions in an inert organic solvent such as dimethylformamide, dimethylacetamide, tetrahydrofuran, or acetonitrile in the presence of a base eg. sodium hydride. Examples of such carboxy-substituted alkyl groups $Z'$ are carboxymethyl, 2-carboxyethyl, 2-carboxyprop-2-yl, 3-carboxypropyl, 3-carboxybut-3-yl and 2-(carboxymethyl)prop-2-yl. Preferably, the free oxime of the α-oximino-acetic acid benzothienyl side chain is alkylated with the carboxy-substituted alkyl halide and the derivative obtained is used to acylate the desired 7-amino nucleus compound by one of the acylation methods described hereinabove. Examples of carboxy-substituted cycloalkyl groups are 1-carboxycyclobut-1-yl, 1-carboxymethylcyclobut-1-yl, 1-carboxycyclopent-1-yl, and 1-carboxycyclohex-1-yl.

Preferred compounds of the invention are represented by the formula 3 when R and $R_1$ are hydrogen, $Z'$ is methyl or 2-carboxyprop-2-yl, $R_2$ is methyl, chloro, or methoxy and the oximino group is syn. Other preferred compounds are represented when R is methyl, and $R_1$ is hydrogen, hydroxy, or chloro. An example of a preferred compound is 7β-[2-(benzothien-4-yl)-2-syn-methoxyiminoacetylamino]-3-methyl-3-cephem-4-carboxylic acid.

The benzothienylglycine compounds and the dihydro derivatives thereof employed in the acylation of the 7-amino nucleus compounds are obtained with a benzothienylglyoxylic acid ester represented by the formula

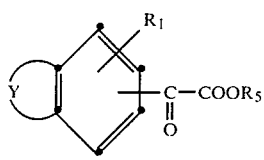

wherein $R_5$ is $C_1$–$C_4$ alkyl and Y, R and $R_1$ have the same meanings as defined for formula 1. The glyoxylic ester derivative is converted to an oxime with hydroxylamine or to an O-substituted oxime with an O-substituted hydroxylamine e.g. methoxyamine. The oxime or O-oxime is then reduced to the glycine ester, by catalytic hydrogenation over palladium on carbon catalyst, or preferably with zinc dust and formic acid, and the glycerine ester is saponified to the glycine. The foregoing is illustrated with a benzothienylglycine, $Y=$—S—CH═CH—, in the following reaction scheme.

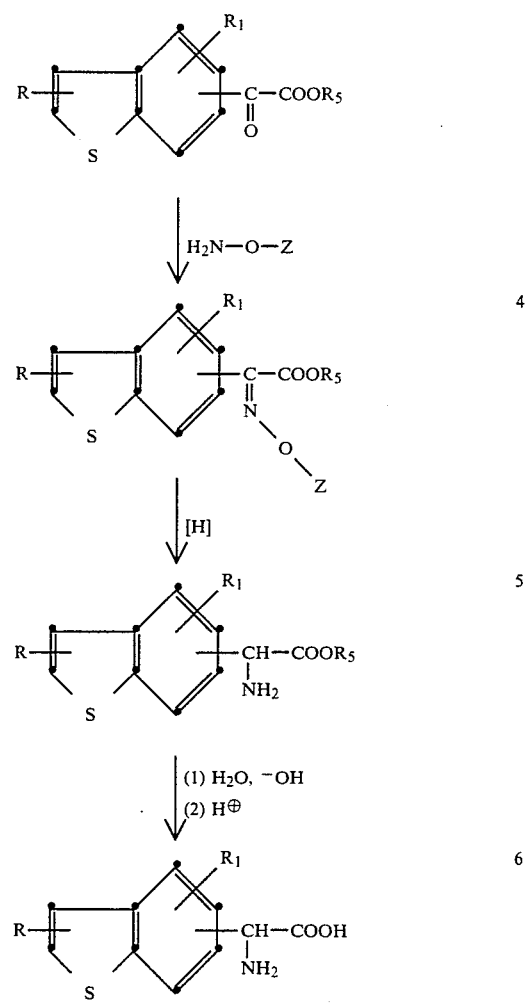

In the above formulae R, $R_1$, and $R_5$ have the same meanings as defined hereinabove and Z is hydrogen or $C_1$–$C_4$ alkyl.

Alternatively, the benzothienylglycine and dihydrobenzothienylglycine compounds are prepared with an acetic acid ester represented by the formula 7

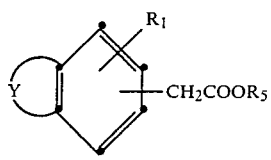

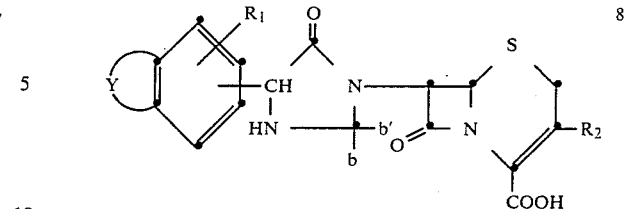

The acetic acid ester is reacted in ethyl alcohol at a temperature of between about −50° C. and about 0° C. with n-butyl nitrite and sodium ethylate to form the oxime 4. The oxime is then reduced as described above and the ester 5 saponified to provide the benzothienyl glycine 6 or dihydrobenzothienylglycine. Prior to use in the acylation of a 7-amino nucleus compound, the amino group of 6 is desirably protected with a conventional amino-protecting group such as defined hereinabove in connection with the description of the acylation. Likewise, the hydroxy group of the oxime 4 is desirably protected in the acylation of a nucleus compound to form compound 2. For example, the oxime hydroxy group may be protected with an acyl group eg. chloroacetyl, or with an alkyl or substituted alkyloxycarbonyl group such as the t-BOC group.

The benzothienylglycyl and dihydrobenzothienylglycines compound 6, as stated hereinabove, can be in the D-, L- or D,L- form. Preferably, the ester 5 or free acid 6 is resolved or epimerized to the desired D-isomer and then used in the acylation. The resolution is carried out eg. with dibenzoyltartaric acid by the method of Lorenz, U.S. Pat. No. 3,832,388 or by epimerization via the benzalimine by the method of Clark and Elks, U.S. Pat. No. 3,976,680. The separation of the D and L isomers also can be carried out enzymatically by the procedure described in Methods in Enzymology, 44, 746 (1976). According to this method the D,L-mixture as the N-chloroacetyl derivative is passed over a column packed with DEAE sephadex containing the enzyme N-acyl-L-aminoacid amidohydrolase. The L-N-chloroacetyl substrate is hydrolysed by the enzyme while the D-N-chloroacetyl derivative is not and is eluted as such with about 0.1M potassium hydrogen phosphate buffer (pH ca. 7.08). The desired D-N-chloroacetylglycine is then chemically hydrolysed to the 2-amino-2-(benzothienyl)acetic acid or ester or the 2-amino-2-(2,3-dihydrobenzothienyl)acetic acid or ester.

The oximino cephalosporins, formula 3, preferably have the oximino group as the syn isomer although the anti isomer also possesses significant antibacterial activity. The desired isomer is obtained with the oximino acid 4 of the desired configuration. The syn and anti forms of the oximino acid 4 may be obtained with the isomeric mixture by chromatography, especially $C_{18}$ HPLC.

In a further aspect of this invention, there are provided cyclic derivatives of the benzothienylglycyl (or 2,3-dihydrobenzothienyl) cephalosporins of the invention (formula 1) represented by the following formula 8

In the formula 8, Y, R, $R_1$, and $R_2$ have the same meanings as defined hereinabove and b, and b' are independently $C_1$–$C_4$ alkyl. The cyclic derivatives are useful precursor compounds of the formula 1 glycines which are converted in vivo to the formula 1 compounds upon absorption.

In the above formula, $C_1$–$C_4$ alkyl refers to methyl, ethyl, n-propyl, isopropyl, and n-butyl. The compounds, named generically herein as 7β-(2,2-dialkyl-5-oxo-4-benzothienyl- or 4-(2,3-dihydrobenzothienyl)-1-imidazolidinyl)-3H(or substituted)-3-cephem-4-carboxylic acids, are prepared by the condensation of a dialkyl ketone with the compound of formula 1 in the presence of a small amount of an acid such as p-toluenesulfonic acid or methanesulfonic acid. The rate of dehydration may be increased by heating the reaction mixture. The condensation is carried out in a suitable solvent which may be an excess of the ketone used to form the cyclic derivative. Ketones which can be used in the condensation are eg. acetone, diethyl ketone, methylethyl ketone, methyl-n-propyl ketone, and like ketones.

Preferred compounds of the formula 8 are represented when b and b' are methyl, for example, 7β-[2,2-dimethyl-5-oxo-4-(benzothien-4-yl)-1-imadazolidinyl]-3-methyl-3-cephem-4-carboxylic acid, and 7β-[2,2-dimethyl-5-oxo-4-(4-hydroxybenzothien-7-yl)-3-chloro-3-cephem-4-carboxylic acid.

This invention also provides pharmaceutical formulations comprising the antibiotics represented by the formulae 1, 3, and 8. According to this aspect of the invention, the antibiotic compound of the formula 1 or its cyclic derivative 8 and the pharmaceutically acceptable salts thereof may be formulated into suitable dosage forms eg. capsules, pulvules, tablets or liquid suspensions suitable for oral administration. The composition may also contain an excipient, antioxidant, stabilizer, lubricant, suspending agent and the like. Such formulations may contain starch, or a sugar such as sucrose, glucose or mannose. Suspensions may contain a flavoring agent, buffer, suspending agent and the like. Suitable dosage forms comprise gelatin capsules containing 250 mg. or 500 mg. of the antibiotic.

The oximino compounds represented by the formula 3, may also be prepared in suitable dosage form for parenteral administration. For example, the compound may be formulated in hermetically-sealed vials or in sterile rubber-stoppered ampoules for i.m. or i.v. administration. Likewise, the oximino compounds may be formulated in plastic bags (pouches) for i.v. administration by the drip method. For such usage the antiobiotic is formulated or mixed with a physiologically acceptable fluid such as Water-for-Injection, 5% dextrose, or 0.9% saline. Suitable parenteral dosage forms of the oximino cephalosporins 3 comprise 250 mg of the antibiotic as the sodium salt in a glass ampoule. Another comprises 500 mg of the potassium salt in a glass ampoule.

The present invention is further illustrated by the following Examples. The Examples are not to be construed as limiting of the description and exemplification of the invention as described hereinbefore.

EXAMPLE 1

7β-[D-2-Amino-2-(benzothien-4-yl)acetylamino]-3-methyl-3-cephem-4-carboxylic acid A suspension of 25 mg of α-t-butyloxycarbonylamino-α-(benzothien-4-yl)acetic acid and 18 mg of EEDQ in 3 ml of acetonitrile was sonicated for 3 minutes and then added to a solution of 26 mg of p-nitrobenzyl 7-amino-3-methyl-3-cephem-4-carboxylate in 30 ml of acetonitrile maintained at 0° C. The acylation mixture was stirred for about 5 hours. Thin layer chromatography on an aliquot of the mixture showed that the acylation was complete. The reaction mixture was added to the reaction mixture of a larger scale acylation carried out with 770 mg of 7ADCA pNB ester, 670 mg of the α-t-BOC amino-(benzothien-4-yl)acetic acid and 500 mg EEDQ in acetonitrile in substantially the manner described above. The combined reaction mixtures were evaporated to dryness to an oil. The oil was dissolved in ethyl acetate and the solution washed with a saturated solution of sodium bicarbonate and then with 1N hydrochloric acid. The solution was dried over magnesium sulfate and evaporated to dryness to yield 1.3 g (87% yield) of p-nitrobenzyl D,L-7β-[2-(t-butyloxycarbonylamino)-(benzothien-4-yl)acetylamino]-3-methyl-3-cephem-4-carboxylate.

The amino-protected and esterified acylation product (1.3 g in THF) was hydrogenated for one hour at room temperature over 2.0 g of prereduced 5% Pd/c under 55 psi hydrogen pressure. After the deesterification was complete, the reduction mixture was filtered and evaporated to an oil. The oil was dissolved in a mixture of ethyl acetate and pH 7 buffer. The pH was adjusted to 8 and the aqueous layer separated. The organic layer was extracted with aqueous sodium bicarbonate and the extract was combined with the aqueous (pH 8) layer. The Ph of the combined aqueous layers were acidified to pH 2.3 and extracted with ethyl acetate. The extract was dried over magnesium sulfate and evaporated to dryness to yield 0.9 g of D,L-7β-[2-(t-butyloxycarbonylamino)-(benzothien-4-yl)acetylamino-3-methyl-3-cephem-4-carboxylic acid. The tlc showed the product as one spot material.

The amino-protected deesterified product, 0.9 g, was treated with 5 ml of trifluoroacetic acid to remove the t-BOC group. The acid solution was diluted with water and the pH of the solution was adjusted to 6.0 with ammonium hydroxide. The solution was then lyophilized to the title compound as a crude solid.

The solid product was dissolved in acetonitrile:water, 9:1, v:v, and the pH of the solution was adjusted to 6.0. The product crystallized from the solution as white crystals. The crystals were collected by filtration and dried overnight under vacuum.

NMR (d trifluoroacetic acid): signals at 2.33 (s, 3H), 3.34 (d, J=8 Hz, 2H), 3.46 (d, J=8 Hz, 2H), 4.12 (s, 1H), 5.20 (d, J=4 Hz, 1H), 5.80 (d, J=4 Hz, 1H), and 7.5–8.2 (m, 5H) delta.

The product was evaluated for antibacterial activity against representative strains of gram positive bacteria by the agar dilution method. Table I below lists the minimum inhibitory concentrations in micrograms over milliliter of both the title compound and cephalexin vs. staphylococci, streptococci and H. influenzae strains.

TABLE 1

Antibacterial Activity Title Compound

| Test Microorganism | Strain | Test Compound[1] A[2] | B[3] |
|---|---|---|---|
| Staphlococcus aureus | X1.1 | 2 | 4 |
| Staphlococcus aureus | V41 | 16 | 128 |
| Staphlococcus aureus | X400 | 64 | 128+ |
| Staphlococcus aureus | S13E | 16 | 128 |
| Staphlococcus epidermidis | EPI1 | 16 | 32 |
| Staphlococcus epidermidis | 222 | 8 | 8 |
| Streptococcus pyogenes | C203 | .25 | .5 |
| Streptococcus pneumoniae | Park I | 1 | 2 |
| Streptococcus group D | X66 | 64 | 128 |
| Streptococcus group D | 2041 | 32 | 128 |
| Haemophilus influenzae | C.L. | 4 | 8 |
| Haemophilus influenzae | 76 | 2 | 8 |

[1] Numerical values are mic in mcg./ml.
[2] A = 7β-[D-2-Amino-2-(benzothien-4-yl)acetylamino]-3-methyl-3-cephem-4-carboxylic acid.
[3] B = cephalexin-7β-(D-2-amino-2-phenylacetylamino)-3-methyl-3-cephem-4-carboxylic acid.

EXAMPLE 2

7β-[2-Amino-2-(3-methylbenzothien-7-yl)acetylamino]-3-methyl-3-cephem-4-carboxylic acid To a solution of 1.050 g of p-nitrobenzyl 7-aminodesacetoxycephalosporanate in 300 ml of dry acetonitrile cooled to 0° C. and maintained under nitrogen was added a solution of 921 mg of a α-t-butyloxycarbonylamino-α-(3-methylbenzothien-7-yl)acetic acid in 75 ml of dry acetonitrile containing 741 mg of EEDQ. The reaction mixture was stirred overnight under a drying tube and then evaporated to dryness. The residual oil was dissolved in ethyl acetate and the solution washed with 1N hydrochloric acid and a saturated solution of sodium bicarbonate, dried, and evaporated to dryness to provide 1.62 g of crude product as an oil.

The product was deesterified with prereduced 5% palladium on carbon catalyst as follows. The ester, 1.62 g, was dissolved in 75 ml of THF and a suspension of 1.62 g. of 5% Pd/c in 40 ml of methyl alcohol (prereduced under 54 psi H₂ for 30 minutes) was added to the solution. The reduction was carried out at room temperature for 45 minutes under 56 psi hydrogen pressure. The reduction mixture was filtered and the filtrate evaporated to dryness. The crude product was dissolved in ethyl acetate-water and the pH of the mixture adjusted to 7.8. The aqueous layer was separated, washed with ethyl acetate and acidified to pH 2.2. The deesterified product was extracted from the aqueous with ethyl acetate and the extract dried, and evaporated to yield 0.72 g of the amino-protected (t-BOC) free acid.

The product was deblocked by treatment with 8 ml of trifluoroacetic acid for 5 minutes. The reaction mixture was diluted with 100 ml of water and the pH adjusted to 7.0 with dilute ammonium hydroxide. The solution was then filtered and chromatographed on a g/aters associates reverse phase C₁₈ silica HPLC using as gradient 0–20% acetonitrile-1% acetic acid-water. Multiple fractions were collected and lyophilized. Fractions 33–37 were combined and contained the L isomer (side chain asymmetric center) and fractions 29–31 contained the D isomer.

We claim:

1. A compound of the formula

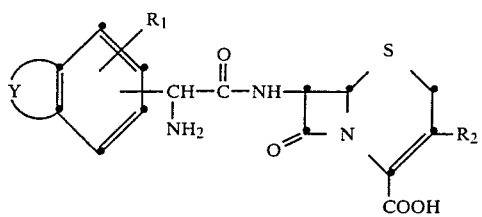

wherein Y is

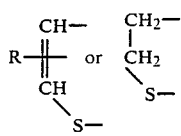

R is hydrogen, $C_1$-$C_3$ alkyl, halogen, nitro, amino, $C_1$-$C_4$ alkoxy, $C_1$-$C_4$ alkanoylamino, or $C_1$-$C_3$ alkylsulfonylamino;

$R_1$ is hydrogen, $C_1$-$C_3$ alkyl, halogen, hydroxy, or $C_1$-$C_4$ alkoxy;

$R_2$ is hydrogen, halogen, methoxy or vinyl, and the pharmaceutically acceptable non-toxic salts thereof.

2. The compound of claim 1 wherein Y is

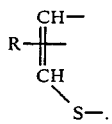

3. The compound of claim 2 wherein $R_2$ is halogen.
4. The compound of claim 3 wherein $R_2$ is chloro.
5. The compound of claim 4 wherein R is hydrogen, methyl, or chloro and $R_1$ is hydrogen, hydroxy, methoxy or chloro.
6. The compound of claim 2 wherein $R_2$ is methoxy.
7. The compound of claim 2 wherein $R_2$ is hydrogen or vinyl.
8. The compound of claim 1 wherein Y is

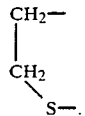

9. A pharmaceutical formulation comprising an antibiotically effective amount of a compound of claim 1 or a pharmaceutically acceptable non-toxic salt thereof and a pharmaceutically carrier.

10. A compound of the formula

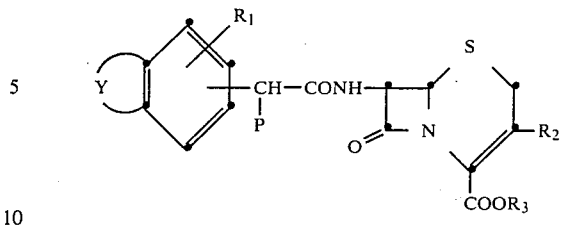

wherein Y is

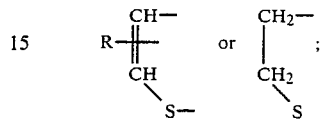

R is hydrogen, $C_1$-$C_3$ alkyl, halogen, nitro, amino, or $C_1$-$C_4$ alkoxy, $R_1$ is hydrogen, halogen, hydroxy, $C_1$-$C_4$ alkoxy, $C_1$-$C_3$ alkyl, $C_1$-$C_4$ alkanoylamino, or $C_1$-$C_3$ alkylsulfonylamino; $R_2$ is hydrogen, halogen, methoxy, or vinyl; P is a protected amino group; and $R_3$ is a carboxy-protecting group.

11. The compound of the formula

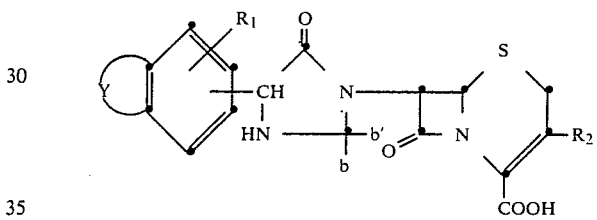

wherein Y is

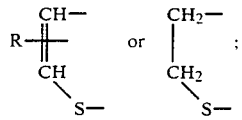

R is hydrogen, $C_1$-$C_3$ alkyl, halogen, nitro, amino, $C_1$-$C_4$ alkoxy, $C_1$-$C_4$ alkanoylamino, or $C_1$-$C_3$ alkylsulfonylamino;

$R_1$ is hydrogen, halogen, hydroxy, $C_1$-$C_4$ alkoxy, or $C_1$-$C_3$ alkyl;

$R_2$ is hydrogen, halogen, methoxy, vinyl;

b and b' are independently $C_1$-$C_4$ alkyl; and the pharmaceutically acceptable non-toxic salts thereof.

12. The compound of claim 11 wherein b and b' are both methyl.

13. A pharmaceutical formulation comprising an antibiotically effective amount of a compound of claim 11 or a pharmaceutically acceptable salt thereof and a pharmaceutical carrier.

* * * * *